US005928138A

United States Patent [19]
Knight et al.

[11] Patent Number: 5,928,138
[45] Date of Patent: *Jul. 27, 1999

[54] METHOD AND DEVICES FOR ENDOSCOPIC VESSEL HARVESTING

[75] Inventors: Gary W. Knight, West Chester, Ohio;
Julia C. Taylor, Seattle, Wash.;
Michael F. Clem, Maineville, Ohio;
Felmont F. Eaves, III, Stone Mountain;
Alan B. Lumsden, Atlanta, both of Ga.

[73] Assignee: Ethicon Endo-Surgery, Inc., Cincinnati, Ohio

[*] Notice: This patent is subject to a terminal disclaimer.

[21] Appl. No.: 08/944,856

[22] Filed: Oct. 6, 1997

Related U.S. Application Data

[63] Continuation of application No. 08/698,499, Aug. 15, 1996, Pat. No. 5,722,934.

[51] Int. Cl.⁶ ........................................ A61B 1/22
[52] U.S. Cl. .................... 600/201; 600/104; 600/210; 600/235; 606/190
[58] Field of Search ................... 600/104, 163, 600/164, 168, 177, 176, 190, 191, 201, 210, 212, 235, 204, 241, 245, 247, 248; 606/159, 190

[56] References Cited

U.S. PATENT DOCUMENTS

| | | | |
|---|---|---|---|
| 1,246,338 | 11/1917 | Smit | 600/212 X |
| 2,831,480 | 4/1958 | Milano | 600/210 X |
| 2,840,070 | 6/1958 | Tofflemire | 600/248 X |
| 2,944,552 | 7/1960 | Cannon | 128/305 |
| 3,495,593 | 2/1970 | Snyder | 600/190 X |
| 3,651,800 | 3/1972 | Wilbanks | 600/210 |
| 3,776,240 | 12/1973 | Woodson | 600/119 |
| 4,232,660 | 11/1980 | Coles | 600/210 |
| 4,793,346 | 12/1988 | Mindich | 128/305 |
| 5,352,219 | 10/1994 | Reddy | 606/190 X |
| 5,373,840 | 12/1994 | Knighton | 128/4 |
| 5,540,711 | 7/1996 | Kieturakis et al. | 606/190 X |
| 5,722,934 | 3/1998 | Knight et al. | 600/201 |

FOREIGN PATENT DOCUMENTS 1371689 2/1988 U.S.S.R. .

OTHER PUBLICATIONS

"Endoscopic Subfascial Discussion of Perforating Veins", (G. Hauer et al., Surg Endosc (1988) 2: 5–12).
"A quick and atraumatic method of autologous vein harvesting using the subcutaneous extraluminal dissector", (W.R. Dimitri et al., J. Cardiovasc Surg, 1987; 28:103–11).
"Long Saphenous Vein Harvesting", (W. Meldrum–Hanna et al., Aust. N.Z. J. Surg. 1986, 56, 923–924).
"Vein Harvest", Alan B. Lumsden & Felmont F. Eaves, III, Endoscopic Plastic Surgery (Quality Medical Publishing, Inc. 1995), pp. 535–543).
"Endoscopic Plastic Surgery", Snowden–Pencer, Inc. (1993 Brochure).

Primary Examiner—Beverly M. Flanagan
Attorney, Agent, or Firm—Louis J. Capezzuto

[57] ABSTRACT

A method for removing a vessel from a patient's body comprises the steps of identifying the vessel to be removing and providing an incision in the patient's body near the identified vessel. An optical dissector is inserted through the incision and tissue is optically dissected away from the surface of the vessel with the optical dissector. The optical dissector is then withdrawn from the body through the incision. An optical retractor is inserted into the body through the incision and is used to retract the dissected tissue away from the surface of the vessel thereby providing space between the dissected vessel and the retracted tissue. The vessel and its side branches are then dissected, ligated and transected and the vessel is then removed from the body through the incision.

6 Claims, 13 Drawing Sheets

METHOD AND DEVICES FOR ENDOSCOPIC VESSEL HARVESTING

This is a continuation of application Ser. No. 08/698,499 filed Aug. 15, 1996, now U.S. Pat. No. 5,722,934 which is hereby incorporated by reference.

FIELD AND BACKGROUND OF THE INVENTION

The present invention relates, in general, to vessel harvesting and, in particular, to a new and useful endoscopic method for harvesting a vessel and the novel instrumentation that is utilized in carrying out the method in support of a surgical procedure such as a coronary bypass procedure or other type of vessel harvest procedure.

Generally, minimally invasive or endoscopic vessel removal and harvesting is known in the surgical field. SU 1371689 teaches a vessel removal procedure which utilizes an endoscope having a lumen therethrough. In this procedure, the small saphenous vein is grasped and held with a grasper which is introduced through the lumen of the endoscope. After connective tissue has been dissected from around the vein, the vein is then ligated and transected and removed from the lower limb of the patient through the lumen of the endoscope.

Essentially the same technique for removal of a vessel is disclosed in U.S. Pat. No. 5,373,840 which pertains to a method for harvesting a vessel such as the saphenous vein. This procedure also utilizes an endoscope having a lumen therethrough which permits the saphenous vein to be grasped by a grasping instrument and dissected. As the vein is withdrawn into the lumen of the endoscope, the endoscope is maneuvered along the length of the vein while side branches of the vein are ligated and transected whenever encountered.

Although this method provides for a minimally invasive technique, there are several drawbacks associated with this procedure. First, in practicing this method there is limited visibility of the saphenous vein and its side branches because viewing is limited to the immediate area directly in front of the endoscope. Secondly, the illumination within the subcutaneous space created by this type of endoscope is also limited to the light emitted directly at the distal portion of the endoscope. Another drawback to this type of procedure is that the side branches of the saphenous vein limit the maneuverability of the endoscope since the outer edge of the endoscope body is prevented from advancing along the trunk of the saphenous vein until the encountered side branches are ligated and transected thereby. Once freed, the endoscope is then maneuvered until the next side branch is encountered. Moreover, it has been found that methods which utilize this type of endoscope, i.e. an endoscope having a lumen, provide a working space which is very restricted because the side walls of the scope body confine the working instrumentation to a limited area.

Furthermore, the vessel harvesting method described above is typically a three-handed approach which actually requires more than one individual. In this method, one hand is required to hold and maintain the endoscope in position, while a second hand is required to hold the free end of the transected vessel with a grasper and a third hand is required to dissect connective tissue away from the vessel.

Another method for harvesting the saphenous vein is disclosed in "Vein Harvest", Alan B. Lumsden and Felmont F. Eaves, III, in Endoscopic Plastic Surgery (Quality Medical Publishing, Inc., 1995), pp. 535–543. This method provides for performing a preliminary dissection of the saphenous vein while using an open technique prior to inserting an endoscopic retractor such as those commonly used in plastic surgery. A typical endoscopic retractor is the Emory Endoplastic Retractor sold by Snowden-Pencer. In this procedure, once the subcutaneous tissue is retracted with the endoretractor, a pair of disposable 5 mm Metzenbaum laproscopic scissors are used to dissect the superior surface of the saphenous vein in order to expose the vein. The speed of the dissection of the saphenous vein in this procedure is limited by the spreading motion of the scissor blades as well as the care which must be exercised by the surgeon when dissecting the vein in this manner.

Presently, there is no known surgical method for harvesting a vessel such as the saphenous vein which addresses the major drawbacks associated with the known methods described above. These drawbacks include excessive time required in removing a section of vessel, limited movement of procedure enabling instrumentation and limited visibility and illumination in the subcutaneous region.

SUMMARY OF THE INVENTION

The present invention pertains to the removal of vessels, and more particularly, to an endoscopic method for removal of a vessel such as the saphenous vein as well as the novel instrumentation which is used to facilitate the method.

It is well known in the surgical field that the saphenous vein, which is located in the leg of a patient, can be utilized as the primary graft material for Coronary Artery Bypass Grafting (CABG) and peripheral grafting procedures.

Up until now, the saphenous vein has been harvested and removed from the leg through open surgical techniques only, e.g. through an incision of substantial length which normally extends from groin-to-knee and knee-to-ankle in the leg of the patient. As can be expected, this type of incision is not only traumatic to the patient but results in morbidity as well as various wound complications.

Since a CABG procedure requires that the removal of the saphenous vein be completed in minimal time, it is imperative that a minimally invasive or endoscopic technique for vein removal be a rapid technique that provides for minimal trauma, is simple to practice and is cost effective.

Accordingly, the present invention meets these requirements by providing a method for removing a vessel from a patient's body, such as the saphenous vein as part of a harvest procedure, wherein the vessel to be removed is identified through any one of a number of known techniques. An incision, normally 3–4 cm, is made in the patient's leg near the identified vessel. An optical dissector is then inserted through the incision and tissue is then optically dissected away from the superior surface of the vessel as the optical dissector is manipulated along the surface of the vessel under direct visualization.

After the initial dissection of the superior surface of the vessel by the optical dissector, the optical dissector is withdrawn through the incision and replaced with an optical retractor which is also inserted through the incision. The optical retractor retracts the dissected tissue away from the superior surface of the vessel thereby creating a subcutaneous space between the dissected vessel and the retracted subcutaneous tissue. While the subcutaneous tissue is maintained in a retracted state, side branches of the vessel are dissected, ligated and transected within the subcutaneous space. Once transected, the vessel is removed through the incision and can be immediately transplanted in a grafting procedure.

The initial dissection made by the optical dissector is an extremely rapid, initial dissection of the superior surface of the vessel. The unique features of the optical dissector allow for this quick initial dissection. The optical dissector comprises a shaft having a lumen therethrough for receiving an endoscope therein and a transparent concave working head connected to a distal end of the shaft. The working head has a spoon-shaped configuration which defines a cavity and allows for blunt dissection of the subcutaneous tissue away from the vessel and, therefore, drastically reduces the chances of damaging the vessel. A handle is connected to the proximal end of the shaft for permitting one-handed use by the surgeon.

The optical retractor according to the present invention comprises an elongated ledge or platform and a shaft having a lumen therethrough connected at an underside of the platform. Similar to the optical dissector, a transparent concave head is connected to the platform at the distal end of the platform. The head also has a spoon-shape and defines a cavity for permitting instrumentation to be inserted therein. The head of the optical retractor not only provides for extremely efficient visibility and illumination, but also provides a working space between the retracted subcutaneous tissue and the superior surface of the vein. Similar to the optical dissector, the spoon-shaped configuration provides for further blunt dissection of the subcutaneous tissue. Instrumentation, more particularly, vessel dissectors, ligating devices and cutting devices, such as scissors, are easily passed through the incision beneath the elongated platform and into the cavity defined by the concave working head for performing complete, circumferential dissection of the vein, as well as ligation and transection of the trunk and side branches of the vein.

The transparent concave head utilized by both the optical dissector and the optical retractor provides for enhanced visibility and illumination in multiple directions, e.g. to include both superior and lateral directions as well as an effective means for achieving blunt dissection of tissue.

It is an object of the present invention to provide a method for harvesting a vessel which is more rapid, efficient and cost effective over known vessel harvesting methods.

It is another object of the present invention to provide an endoscopic method for vessel harvesting which is less traumatic to the patient over known vessel harvesting methods.

It is another object of the present invention to provide an optical dissector which is more effective at dissecting tissue from a vessel over known dissectors currently used in the surgical field.

It is another object of the present invention to provide an optical retractor which is more effective at retracting tissue from a vessel over known retractors currently used in the surgical field.

BRIEF DESCRIPTION OF THE DRAWINGS

Embodiments of the invention are described by way of example with reference to the accompanying drawings, in which:

FIG. 15 is a perspective view of an alternative embodiment for the optical tip which can be affixed directly to the distal end of an endoscope or the like;

FIG. 16 is a side view in partial cross-section of the securent means for the detachable tip portions of FIG. 15.

DESCRIPTION OF THE PREFERRED EMBODIMENTS

Figure 7:
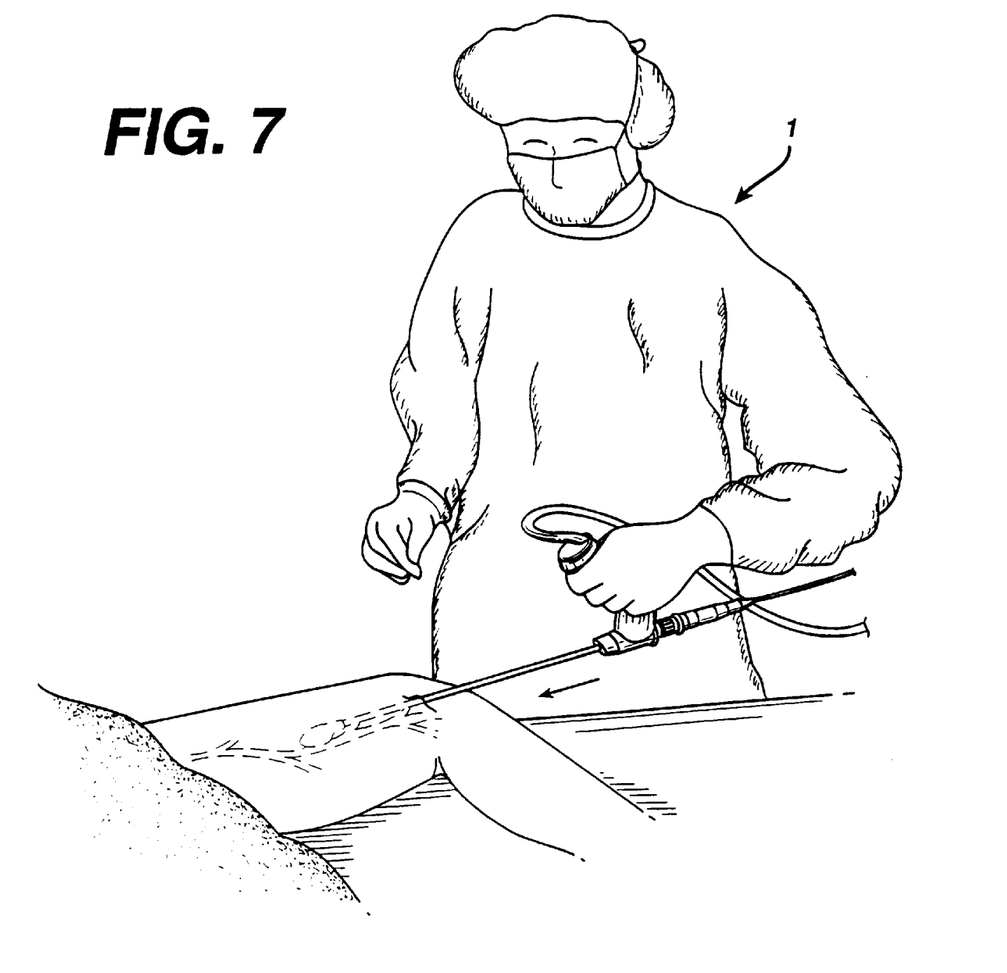
FIG. 7 is a perspective view of the insertion and manipulation of the optical dissector after a first incision has been made according to the method of the present invention.
Figure 8:
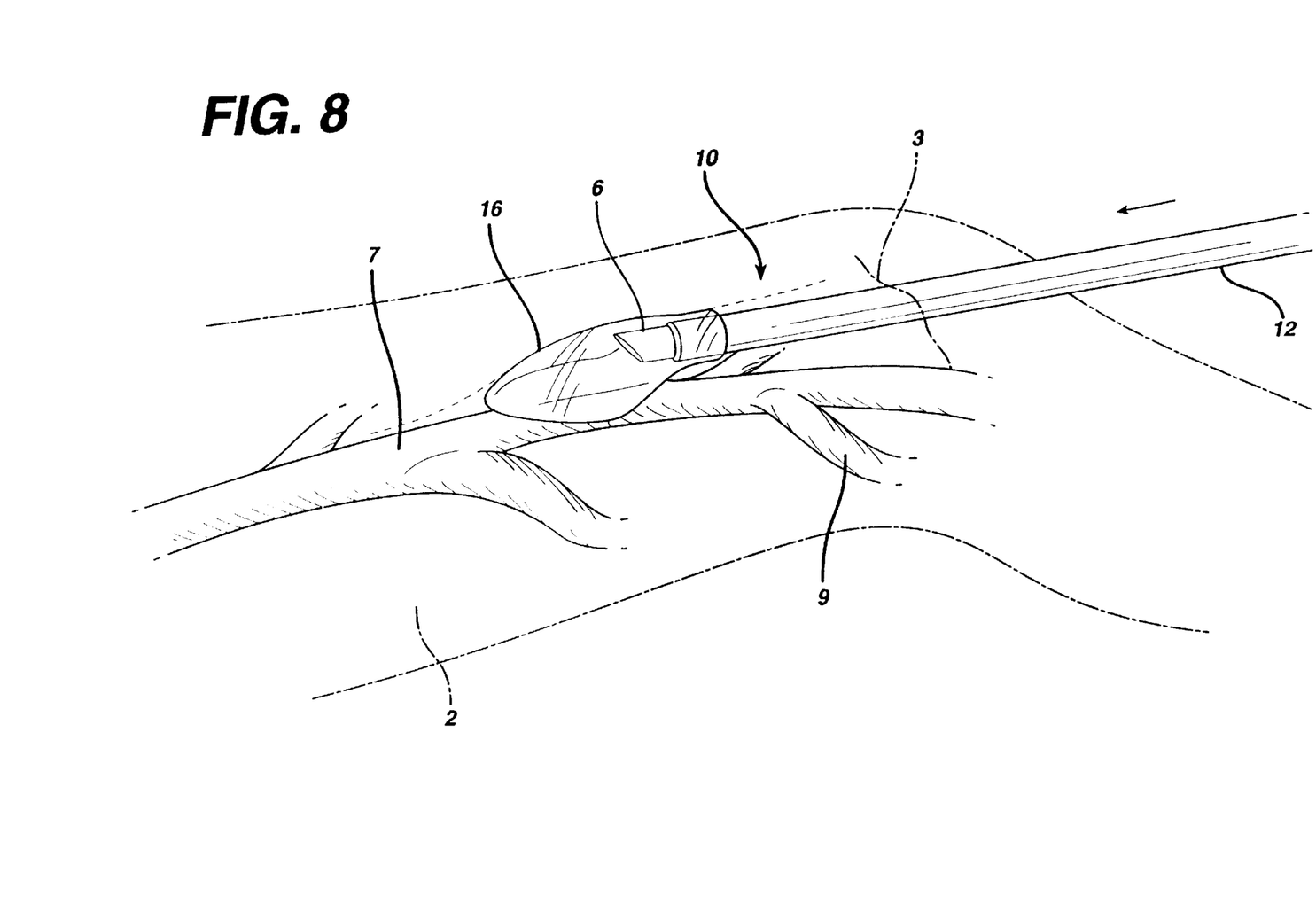
FIGS. 8–14 are enlarged perspective views illustrating the method of endoscopic vein harvesting according to the present invention.

As best shown in FIGS. 7 and 8, the present invention provides for an endoscopic method for removing or harvesting a vessel such as the saphenous vein 7 which is located in a patient's leg 2. Although not required, the patient can be positioned in a dorsal recumbent position with the leg 2 externally rotated to reveal the medial surface of the leg 2. Additionally, the leg 2 may be placed in a "frog leg" position.

In carrying out the method according to the present invention, the surgeon 1 can anatomically identify the saphenous vein 7 through any one of a number of identification techniques which can include preoperative doppler ultrasound scanning of the leg 2 or any other suitable identification technique which will allow definitive determination of the position, size and suitability of the vein 7 prior to harvesting. Preoperative scanning is not a requirement since identification of the saphenous vein can also be conducted visually.

As illustrated in FIG. 8, a skin incision 3 is made near the identified vein 7. The incision 3 is preferably 3–4 cm and can be placed at any desired location including the knee, groin or ankle. After the incision 3 is made, an optical dissector, generally designated 10, is introduced through the incision 3 and is advanced proximally and/or distally along the superior surface of the vein 7 for establishing an initial blunt dissection.

Figures 1, 2:
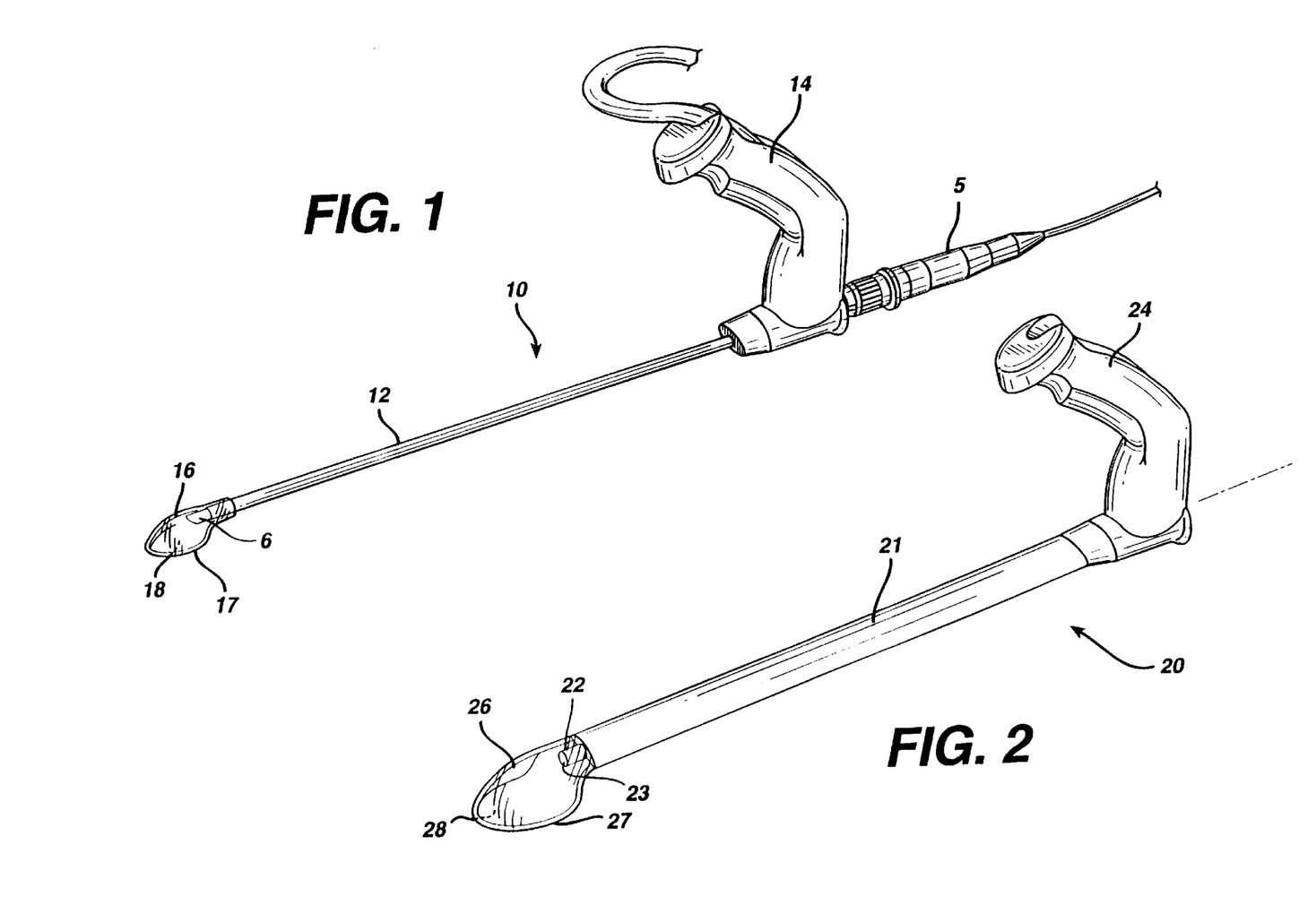
FIG. 1 is a perspective view of an optical dissector according to the present invention shown with an endoscope coupled therewith.
FIG. 2 is a perspective view of an optical retractor according to the present invention.

Referring to FIG. 1, there is shown the preferred embodiment of the optical dissector 10. The optical dissector 10 comprises a shaft 12 having a lumen 13 therethrough, shown in FIG. 4, for receiving an endoscope 5 therein. A concave working head 16 is connected to the distal end of the shaft 12 and has a spoon-shape configuration defining a cavity 18. The working head 16 is made of a transparent material such as plastic for visualization of the blunt dissection of the subcutaneous tissue. Transparent working head 16 has a substantially hemi-spherical profile which permits enhanced visualization and illumination in a 180° area for distal end 6 of the endoscope 5. A handle 14 is connected to the proximal end of shaft 12 for allowing one-handed use and maneuverability. As outer peripheral edge 17 of the optical dissector 10 is advanced over the vein 7, subcutaneous tissue is bluntly dissected away from the vein 7. Because, the working head 16 is made of a transparent material, such as plastic, the direct visualization allows for confirmation of the course of the vein 7 as well as identification of side branches 9.

Once a sufficient plane of dissection has been achieved at the superior surface of the vein 7, the optical dissector 10 is withdrawn from the leg 2 through the incision 3. Then, an optical retractor, generally designated 20, is inserted through the incision 3 at the dissected plane as best illustrated in FIG. 9.

Figures 5, 6:
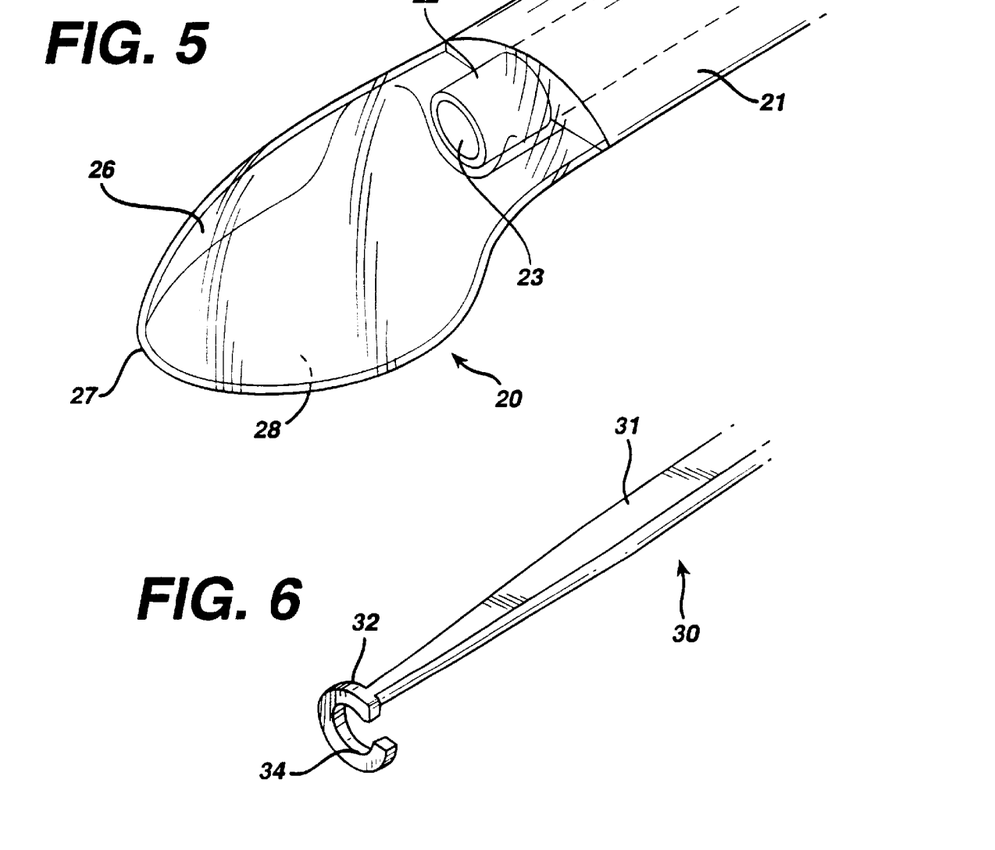
FIG. 5 is an enlarged perspective view of the distal tip portion of the optical retractor.
FIG. 6 is a perspective view of the distal portion of a vessel dissector according to the present invention.
Figure 17:
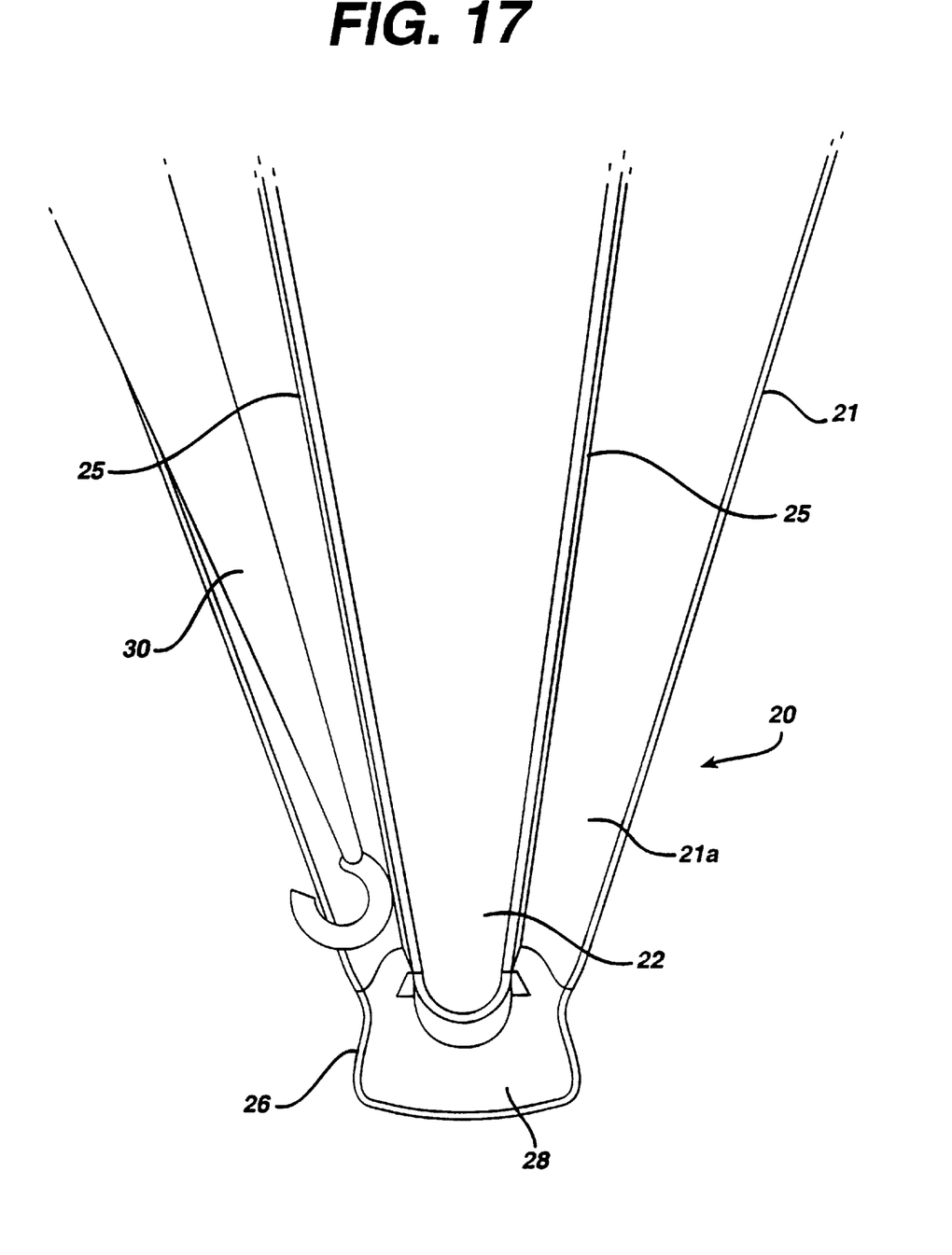
FIG. 17 is a perspective view of the underside of the optical retractor and an instrument therewith.

As illustrated in FIGS. 2, 5 and 17 the optical retractor 20 comprises an elongated ledge or platform 21 having a shaft 22 connected at an underside 21a of the platform 21. The shaft 22 has a lumen 23 extending entirely therethrough for receiving endoscope 5 therein. Tip 6 of endoscope 5, which may be a 30° scope, can extend from shaft 22 into cavity 28 defined by the outer surface configuration of transparent concave head 26 and a continuous outer edge 27. Handle 24 is connected to the elongated platform 21 at the proximal end of the platform 21 for providing one-handed use and permits the retractor 20 to be lifted at any angle with respect to the axis of the vein 7 for creating space beneath the subcutaneous tissue.

Figure 4:
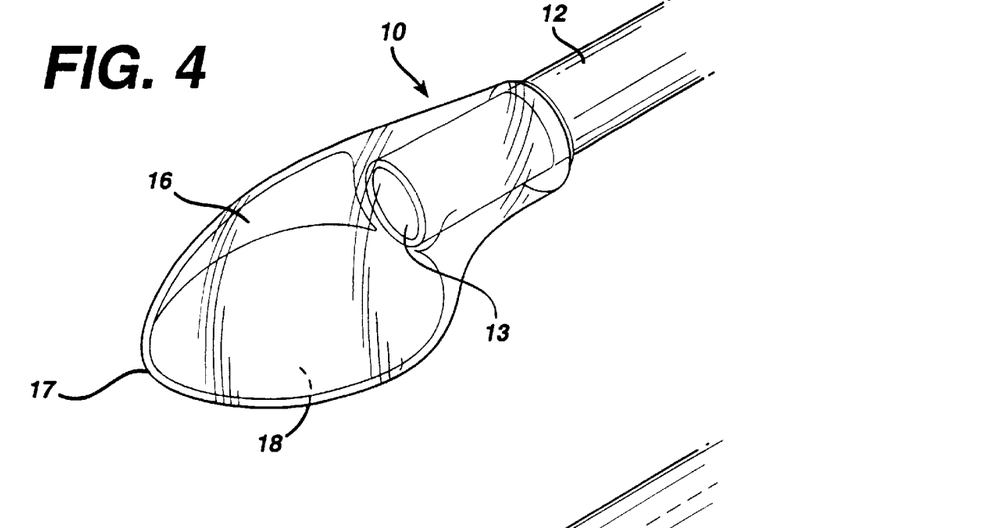
FIG. 4 is an enlarged perspective view of the distal tip portion of the optical dissector.

FIG. 5 shows the transparent working head 26 of the optical retractor 20 with a similar configuration and profile to the working head 16 for the optical dissector 10 illustrated in FIG. 4. Like the dissector working head 16, the retractor working head 26 is made of a transparent material, such as plastic, and has a substantially hemi-spherical or spoon-shape configuration with an outer peripheral edge 27 which defines a cavity 28 thereunder which serves as a working space for the end effectors of procedure enabling instrumentation.

Figure 9:
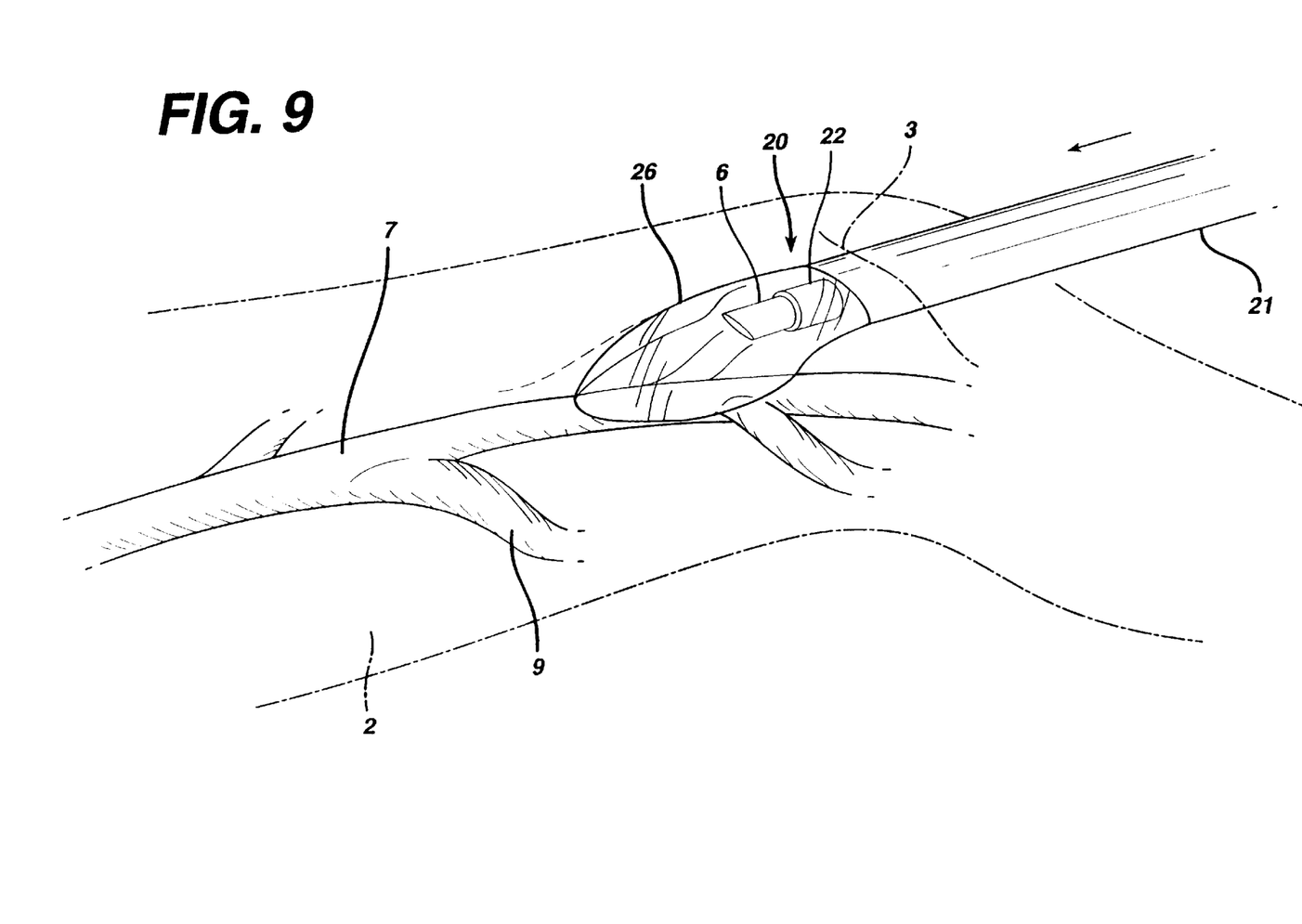
Figure 10:
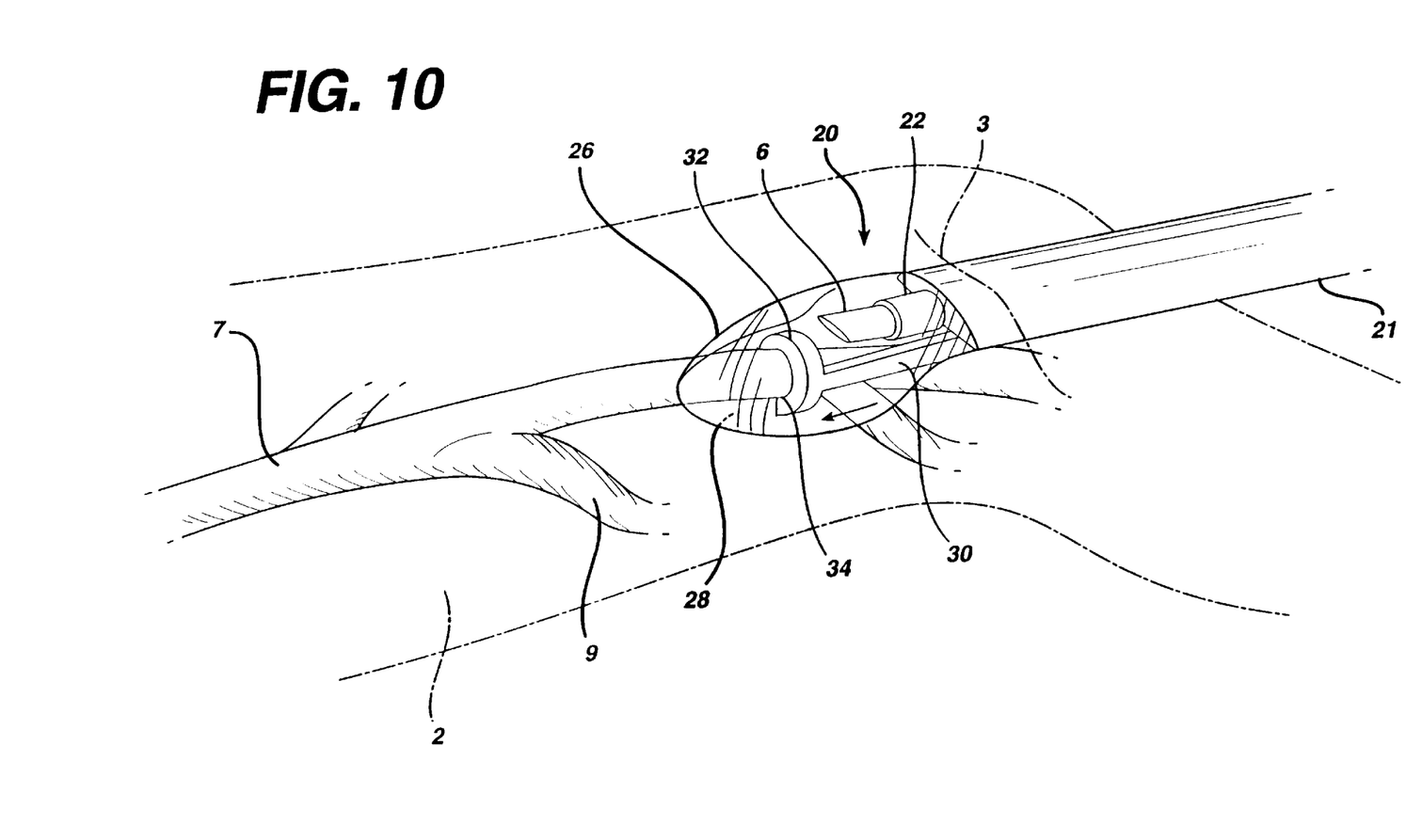
Figure 11:
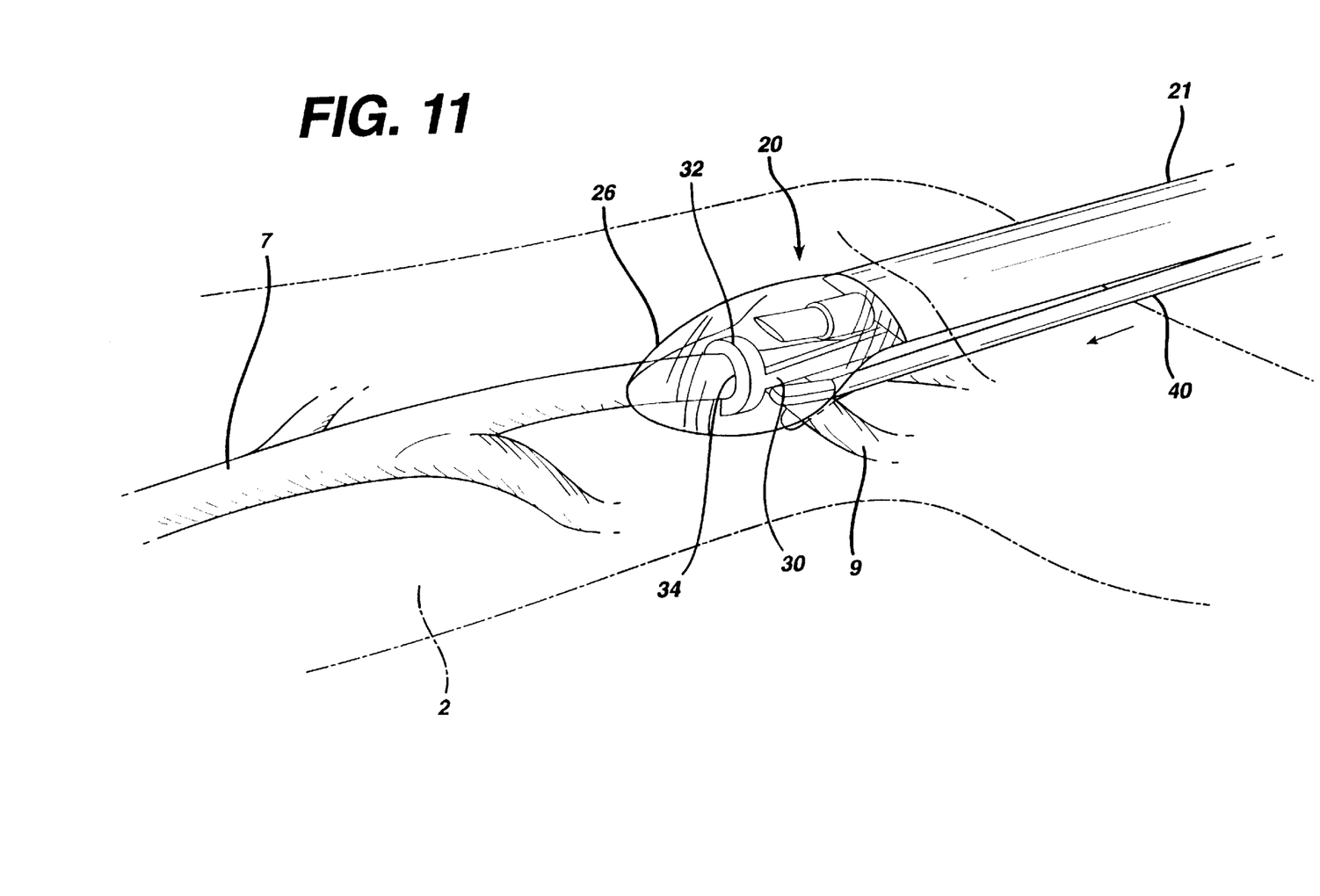
Figure 12:
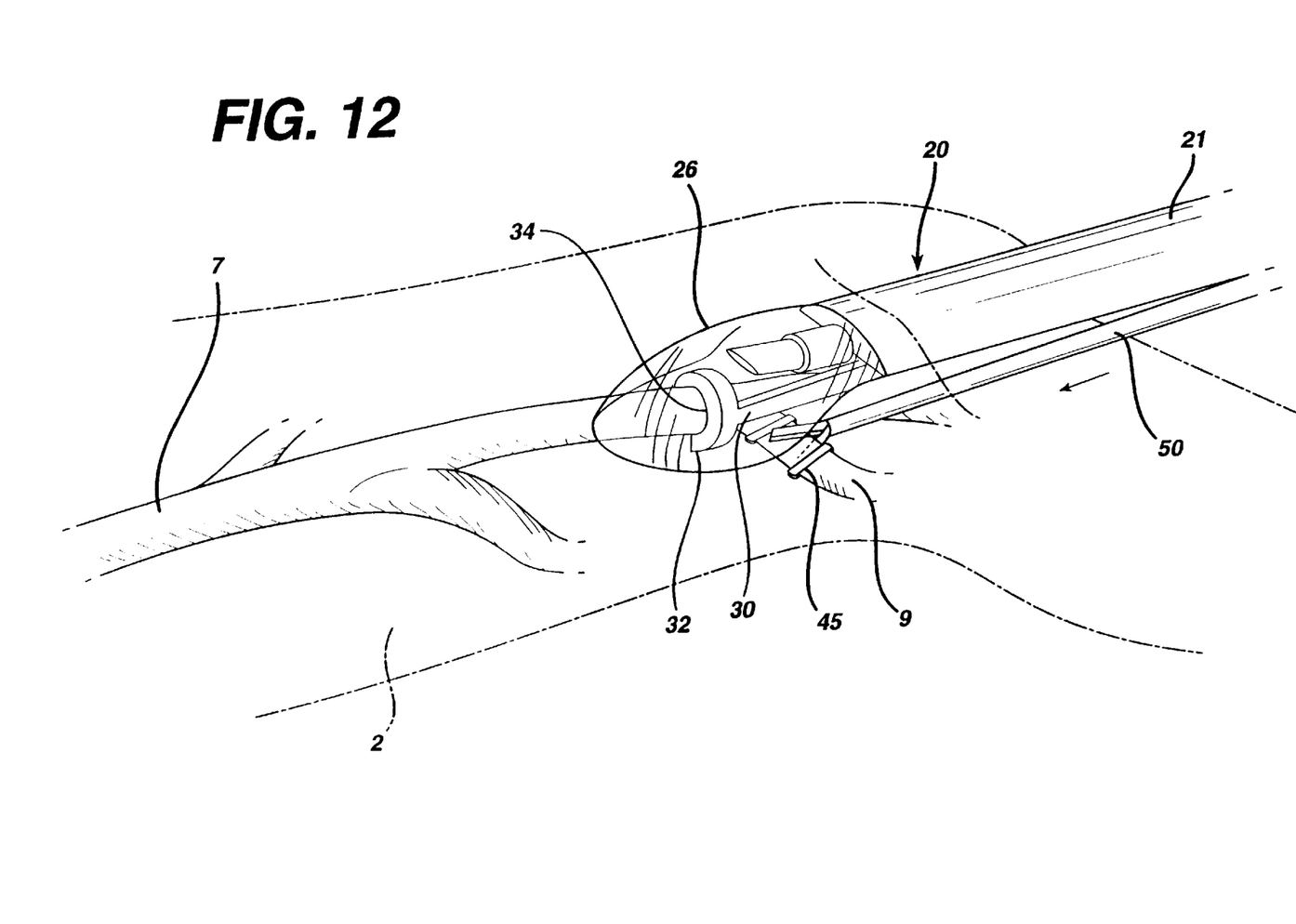

The transparent working head 26 of retractor 20 enhances visualization and illumination over a substantially 180° area projecting from the distal end 6 of the endoscope 5 as shown in FIG. 9. The spoon-shape profile of working head 26 achieves effective dissection and retraction of the subcutaneous tissue. When in use, the retractor 20 is maneuvered beneath the subcutaneous layers and the platform 21 and head 26 maintain space between the retracted layers and the vein 7 for passage of instrumentation beneath the platform 21 and into the cavity 28 as best shown in FIGS. 10–12.

The cavity 28 is a substantially 180° enclosed area which permits instrumentation to be inserted therein due to the unique spoon-shape outer surface configuration of the working head 26. Instrumentation such as a vessel dissector 30, ligating device 40 and cutting device 50 are easily inserted into the subcutaneous space and working cavity 28 created by the optical retractor 20 upon retracting the subcutaneous tissue away from the vessel 7. By manipulating the handle 24 of the retractor 20, the surgeon 1 is able to create a working passage between the retracted subcutaneous tissue and the vein 7.

As illustrated in FIG. 17, the optical retractor 20 has guide rails 25 connected to the underside 21a of the platform 21. The guide rails 25 are located on each side of shaft 22 and extend parallel with the shaft 22. Additionally, guide rails 25 extend away from the underside 21a of the platform 21 at an angle, preferably 90°, and permit an instrument to be abutted against rails 25 for guiding the instrument to the cavity 28. Thus, guide rails 25 provide the surgeon 1 with control over the positioning of the instrumentation.

The vessel dissector 30, as shown in FIG. 6, comprises an elongated shaft 31 and a substantially C-shaped end effector 32 having a blunt dissector edge 34. As shown in FIGS. 10–12, the vessel dissector 30 is advanced along the axis of the vein 7 such that edge 34 is used to perform circumferential blunt dissection of the vein 7 and by manipulating the end effector 32 circumferentially, the blunt dissector edge 34 cleanly dissects connective tissue away from the vein 7. A major advantage of the C-shaped configuration of the end effector 32 is that the end effector 32 can be placed around the vein 7 without having to cut or slice the vein 7 thereby resulting in an effective way to access the vein 7.

Once the vein 7 has been skeletonized, ligating device 40 is introduced into the incision 3 and into the working cavity 28 provided by the configuration of working head 26 in order to ligate side branches 9 of the vein 7. Ligating device 40 can be any type of ligating device such as a clip applier, ligature applier, suture tying device or electrosurgical coagulation device.

Each side branch 9 is ligated with two ligating members, such as clips 45, placed adjacent each other with sufficient spacing therebetween, wherein a cutting device 50, such as a pair of laproscopic scissors, is introduced into the working cavity 28 for transecting the side branch 9 between the clips 45. The ligation and transection of the vein 7 is not limited to the technique described above, but is used to illustrate just one of the numerous techniques available for ligating and transecting vessels.

Figure 14:
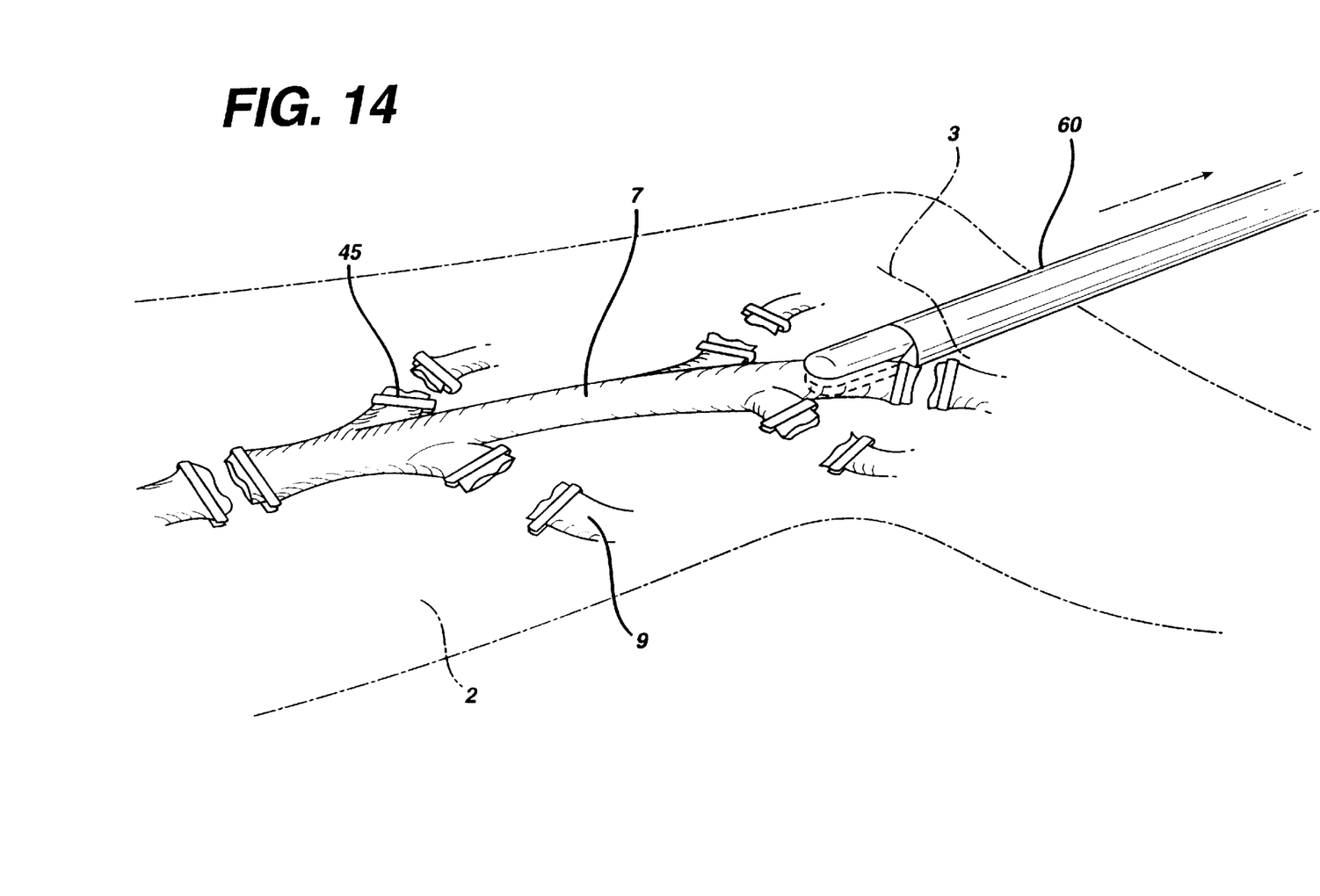

Once a sufficient length of the vein 7 has been ligated and transected, the optical retractor 20 can be withdrawn from the leg 2 through the incision 3. As illustrated in FIG. 14, endoscopic graspers 60 are introduced into the incision 3 and the vein 7 is grasped by graspers 60 for removal and immediate preparation for transplant in a grafting procedure.

Figure 13:
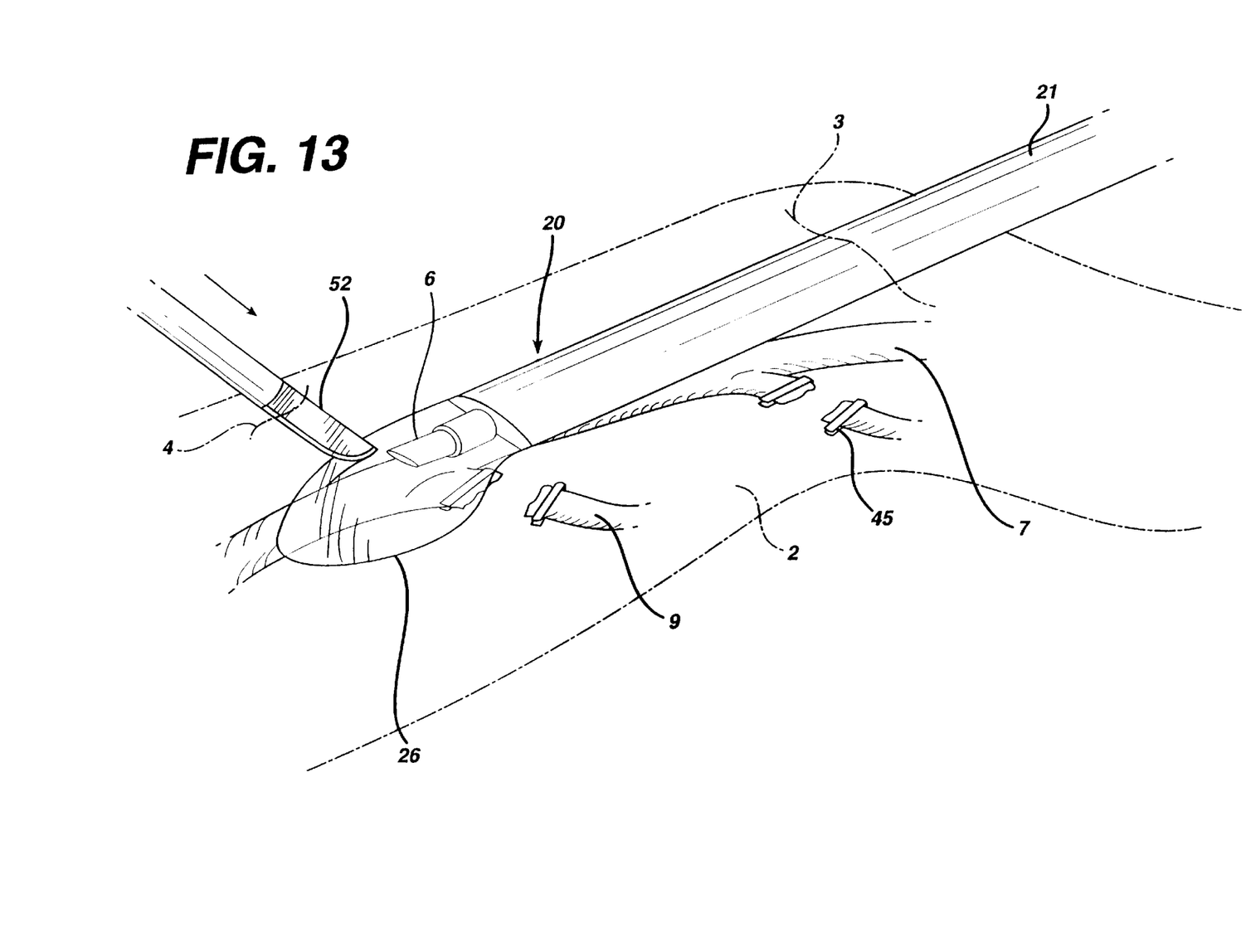

If a substantial length of vein 7 is required to be removed from the leg 2, a transillumination technique, such as the one shown in FIG. 13, can be utilized with the optical retractor 20 for providing a subsequent incision. This subsequent incision permits further optical dissection and optical retraction of the subcutaneous tissue from the vein 7 until the desired length of the vein 7 is achieved. The transillumination technique according to the present invention comprises identifying the transparent working head 26 through the subcutaneous layers of the leg 2 and utilizing a cutting instrument such as a scalpel 52 for making a second incision 4 in the leg 2 at the transparent working head 26. The transparent head 26 enhances the transmission of light from the distal tip 6 of the endoscope 5. Accordingly, the enhanced transillumination provided by the transparent head 26 serves as guide for the placement of the second incision 4. Through the second incision 4, the optical dissector 10 is then reintroduced in order to continue dissection along the vein 7 similar to the initial dissection illustrated in FIGS. 7 and 8.

Although the transected vein 7 is shown in FIG. 14 to be removed through the initial skin incision 3, the transected section of vein 7 can be removed through the initial incision 3, the second incision 4 or any other subsequent incisions.

Figure 3:
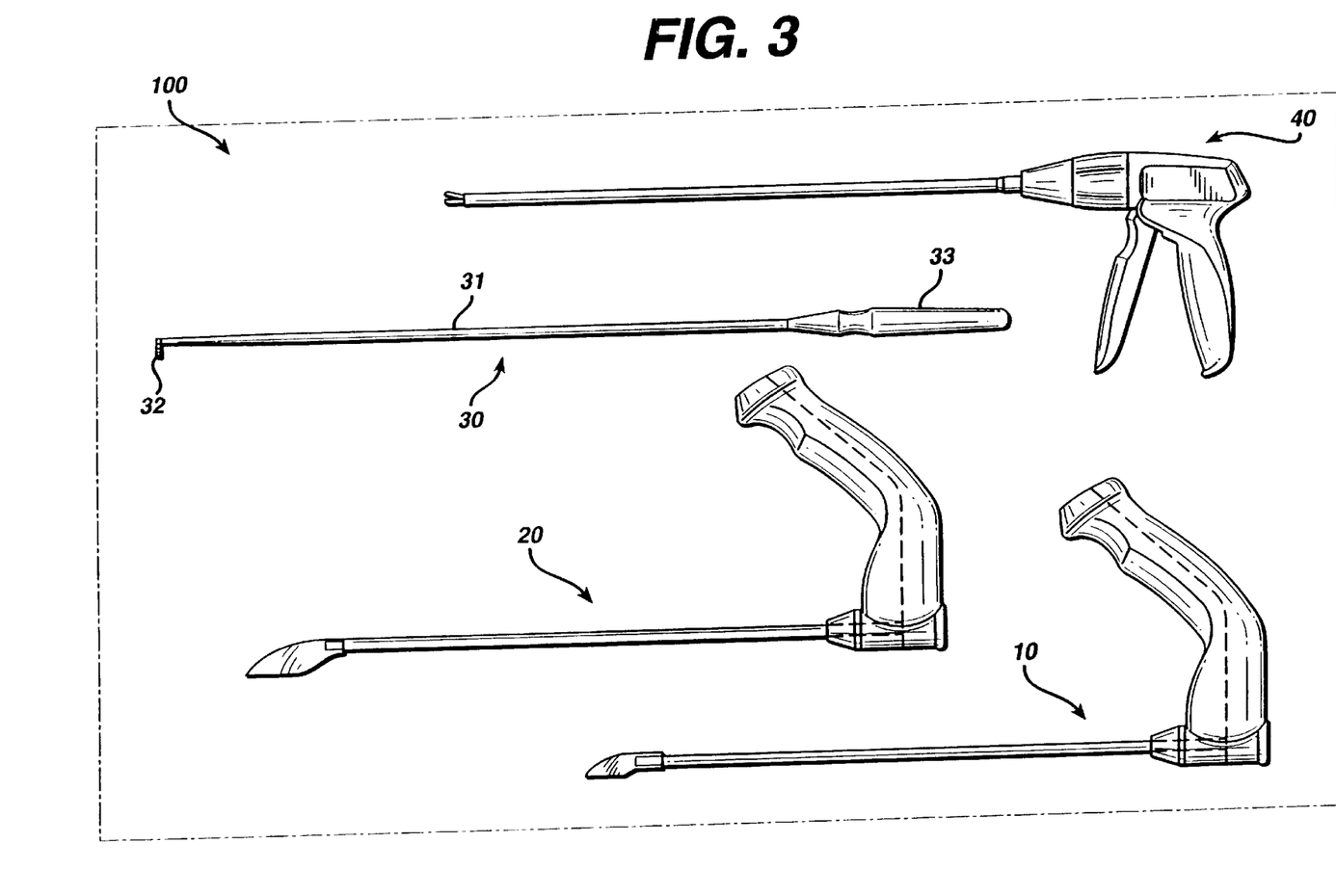
FIG. 3 is a side elevational view of a vessel harvesting kit according to the present invention comprising an optical dissector, an optical retractor, a vessel dissector and a ligation instrument.

In order to facilitate the method described above, a kit 100, as shown in FIG. 3, is provided and comprises the optical dissector 10, the optical retractor 20, the vessel dissector 30 and the clip applier 40. The saphenous vein harvesting kit 100 provides the surgeon with procedure enabling instrumentation in a single presentation.

Figures 15, 16:
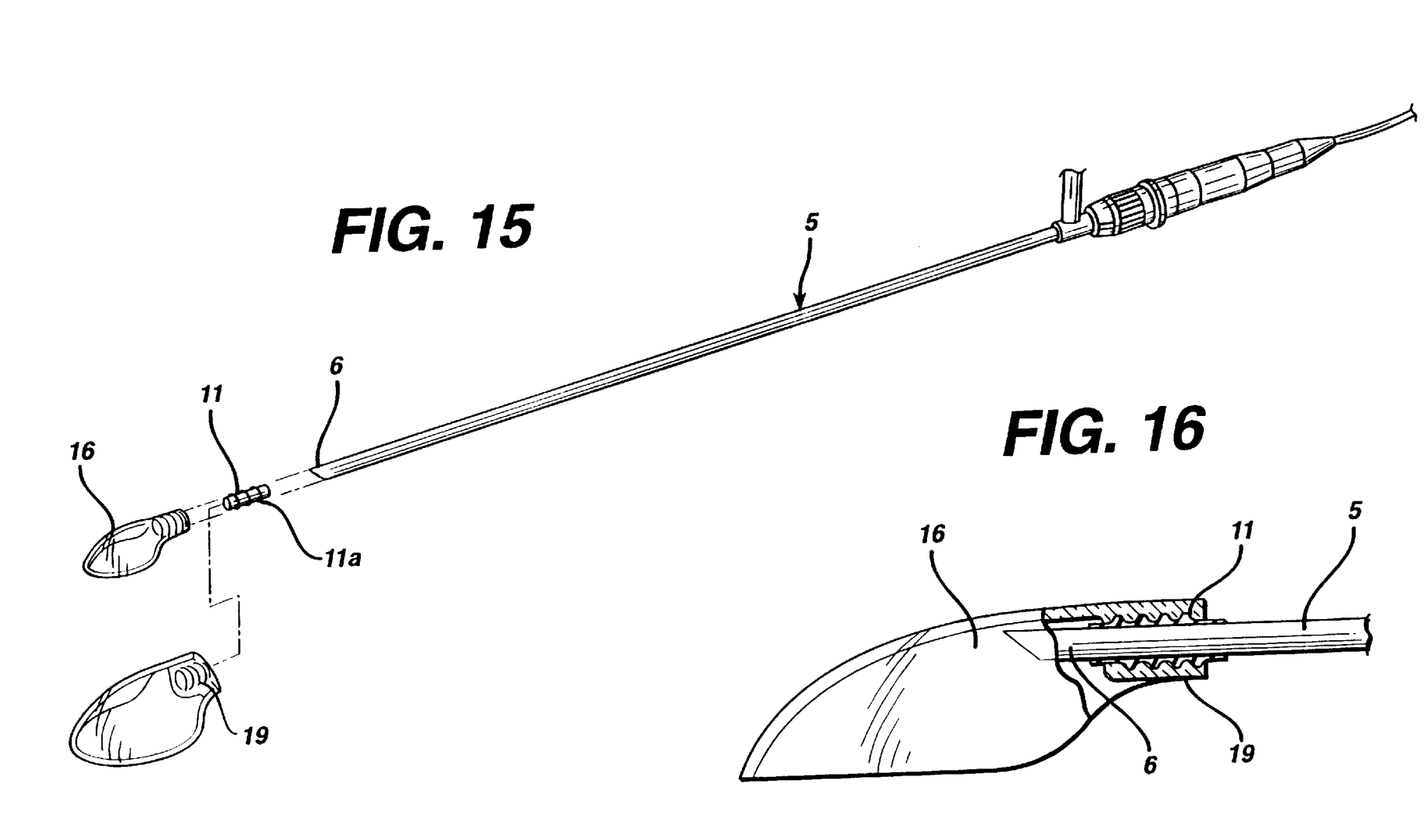

FIGS. 15 and 16 show the transparent working head 16 as a component which can be detachably connected directly to the endoscope 5. The detachable connection of head 16 to endoscope 5 can be accomplished through the use of securing means 11, shown as a latex rubber sleeve, which can be pulled over the distal end 6 of the endoscope 5. The sleeve 11 has a plurality of raised ridges or threads 11a with internal threads 19 formed at the proximal end of the working head 16. Once the working head 16 is threaded onto securing means 11 about distal end 6 of the endoscope 5, as shown in FIG. 16, the working head 16 is firmly secured and can only be removed by unthreading.

Although only one type of securing means is shown in FIGS. 15 and 16 for detachably connecting transparent head 16 to endoscope 5, any type of suitable securing means can be utilized. Thus, the detachable connection feature of the working head 16 of the present invention is not limited to the securing means described above.

Moreover, the working head 26 for the optical retractor 20, although not illustrated, can also be detachably connected in a manner similar to the one described above or like manners well within the level of ordinary skill of one in the surgical field.

Although the working heads 16 and 26 of the optical dissector 10 and optical retractor 20 respectively have been shown and described to be made of a transparent material, such as plastic, the working heads 16 and 26 according to the present invention can also be made of glass or other types of known transparent material.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A surgical device for dissecting and retracting tissue comprising:

an elongated platform;

a working head connected to one end of said elongated platform, said working head having a spoon-shape configuration and defining a cavity therein for accommodating an end effector of an instrument; and means for receiving an endoscope with said elongated platform.

2. The surgical device according to claim 1, including a handle connected to another end of said elongated platform.

3. The surgical device according to claim 2, wherein said means for receiving an endoscope with said elongated platform comprises a shaft connected to said platform, said shaft having a lumen extending therethrough.

4. The surgical device according to claim 3, wherein at least a portion of an endoscope is positionable in said cavity and extending from said shaft.

5. A surgical device for dissecting tissue comprising:

a shaft having a lumen therethrough for receiving an endoscope therein;

a working head connected to one end of said shaft, said working head having a spoon-shape configuration and defining a cavity therein for accommodating an end effector of an instrument.

6. The surgical device according to claim 5, including a handle connected to another end of said shaft.

* * * * *